US 6,732,887 B2

(12) United States Patent
Bills

(10) Patent No.: US 6,732,887 B2
(45) Date of Patent: May 11, 2004

(54) TWO-PART COMPOSITION SYRINGE DELIVERY SYSTEM

(75) Inventor: Dan J. Bills, Salt Lake City, UT (US)

(73) Assignee: Ultradent Products, Inc., South Jordan, UT (US)

(*) Notice: Subject to any disclaimer, the term of this patent is extended or adjusted under 35 U.S.C. 154(b) by 57 days.

(21) Appl. No.: 10/106,602

(22) Filed: Mar. 26, 2002

(65) Prior Publication Data
US 2003/0183653 A1 Oct. 2, 2003

(51) Int. Cl.⁷ .............................. B67D 5/52; A61M 5/19
(52) U.S. Cl. .................... 222/154; 222/137; 222/145.5; 222/145.6
(58) Field of Search ................. 222/154, 158, 222/137, 145.3, 145.5, 145.6; 604/82

(56) References Cited

U.S. PATENT DOCUMENTS

| 2,112,160 A | 3/1938 | Johnson .................... 128/234 |
| 3,194,426 A | 7/1965 | Brown, Jr. ................. 220/23.4 |
| 3,223,083 A | 12/1965 | Cobey .......................... 128/92 |
| 3,269,389 A | 8/1966 | Meurer et al. .............. 128/198 |
| 3,827,602 A | 8/1974 | Nicholls .................... 222/137 |
| 3,828,980 A * | 8/1974 | Creighton et al. .......... 222/137 |
| 4,260,077 A | 4/1981 | Schroeder .................. 222/137 |
| 4,631,055 A * | 12/1986 | Redl et al. .................. 222/135 |
| 4,979,942 A * | 12/1990 | Wolf et al. ................. 222/137 |
| 5,104,375 A * | 4/1992 | Wolf et al. ................. 604/518 |
| 5,290,259 A * | 3/1994 | Fischer ....................... 604/218 |
| 5,464,396 A | 11/1995 | Barta et al. ................. 604/191 |
| 5,582,596 A * | 12/1996 | Fukunaga et al. .......... 222/137 |
| 5,814,022 A | 9/1998 | Antanavich et al. ........ 604/191 |
| 6,132,396 A * | 10/2000 | Antanavich et al. ......... 604/82 |
| 6,234,994 B1 * | 5/2001 | Zinger ......................... 604/82 |
| 6,251,370 B1 * | 6/2001 | Uchida et al. ............... 424/45 |
| 6,443,612 B1 * | 9/2002 | Keller ...................... 222/145.6 |
| 6,499,630 B2 * | 12/2002 | Muhlbauer et al. ......... 222/137 |

* cited by examiner

Primary Examiner—Kenneth Bomberg
(74) Attorney, Agent, or Firm—Workman Nydegger

(57) ABSTRACT

The syringe devices of the invention include detachably connecting barrels and detachably connecting plungers. The barrels can be manufactured at different times and out of different materials to have differing colors, insulating properties, inner diameters, material compositions, and clearness. The syringe devices also include barrel connecting means for detachably connecting the barrels and plunger connecting means for detachably connecting the plungers. In certain embodiments, the syringe devices also include applicator tips configured for thoroughly mixing the components contained in the barrels before being dispensed through the applicator tip.

20 Claims, 8 Drawing Sheets

TWO-PART COMPOSITION SYRINGE DELIVERY SYSTEM

BACKGROUND OF THE INVENTION

1. The Field of the Invention

The present invention is in the field of dispensing devices and, more particularly, in the field of syringe devices configured to mix and dispense mixed compositions.

2. The Relevant Technology

Many reactive compositions are packaged in two parts, often known as "A and B components" or "first and second materials". Upon mixing, the A and B components undergo a chemical reaction that causes the resultant mixed composition to cure in some desired manner. In the dental field, for example, several mixed compositions currently enjoy wide use, such as cements and composite materials. Dental impression materials are also typically made using multiple components.

In order to function properly, the A and B components should be mixed together rapidly, thoroughly and in the appropriate proportions. Failure to mix the components rapidly can result in loss of valuable working time before the resultant mixed composition cures. In addition, failure to mix the components thoroughly or in the appropriate proportions can result in a composition having less than optimum characteristics. For instance, when a dental cement composition is either poorly mixed or includes the wrong proportions of A and B components, the cement can fail to obtain the chemical strength and/or adhesion properties required for a long-term bond.

One method for gauging and controlling the proportion of A and B components included in the mixed composition is to dispense the components from a pair of single dose syringes containing the appropriate proportions of the A and B components. Once dispensed, the components can then be mixed in a conventional manner, such as with a spatula or another stirring device in a mixing bowl or on a mixing pad. This additional mixing procedure, however, tends to be somewhat messy and time consuming. It is also difficult at times to ensure that the mixing has been sufficiently thorough.

Another method for delivering the A and B components is to use an existing double barrel syringe having two integrally connected syringes and a double plunger assembly for dispensing the contents from the barrels. Double barrel syringes are advantageous for enabling the components to be dispensed more quickly than with single syringes and for ensuring the A and B components are dispensed in the appropriate proportions, particularly when the syringes contain multiple doses. For instance, the double barrels of the syringes can be configured with large storage capacities for containing enough of the A and B components to be used for several doses or applications. Because the barrels are integrally connected, and assuming the plunger assembly is configured to dispense the contents from the barrels simultaneously, the appropriate mixing ratios of the components will be preserved regardless of the amount of the components dispensed from each barrel. The barrels of the syringe can also be coupled to an applicator tip, which is generally useful for initiating and facilitating the mixing of the A and B components inasmuch as the components come in contact within the applicator tip and therefore begin mixing before being dispensed.

One problem with existing double barrel syringes, however, is that they are not configured for being filled from the front or from the barrel tips. In particular, front filling existing double barrel syringes from the front can potentially lead to the introduction of the A and B components into the wrong barrels, because of the small size and proximity of the barrel tips. Introduction of the components into the wrong barrels can be problematic because it can result in premature curing of the components within the barrels. Accordingly, it is necessary to fill existing double barrel syringes that are configured with tips in close proximity from their backsides to avoid mixing the components during the filling process. Backside filling, however, may be undesirable because it can result in the formation of bubbles, air pockets and other pressure irregularities within the barrels which can cause spurting, irregular discharge, or otherwise prevent the A and B components from being dispensed in the appropriate proportions.

Pressure irregularities can also cause cross-migration and the premature curing of the A and B components within the opposing barrels. For example, a bubble existing in the A component barrel will be compressed when an adequate force is applied by the plunger assembly for expressing the A and B components. When the plunger assembly is released, however, the bubble within the A component barrel will expand, thereby forcing the plunger assembly to retract and creating a pressure void within the B component barrel. This pressure void naturally creates a suction force at the tip of the B component barrel which is sufficient to cause some of the residual A component to migrate backwards into the B component barrel where it can prematurely mix with the B component, cure, and inhibit or prevent future use of the syringe.

To avoid the aforementioned problems, some existing double barrel syringes are configured with tips that are spaced far apart so that they can be filled from the front. However, this spacing of the barrel tips also prevents the barrels from connecting with certain applicator tips for mixing purposes, thereby requiring the components to be mixed in an additional step after being dispensed from the barrels and prior to application. As mentioned above, this additional mixing step can be both time consuming and messy. Even if the spaced apart barrel tips are able to be connected to a separate mixing tube or tip, the A and B components must traverse interconnecting pathways existing between the barrel tips and the mixing tip before the components can be mixed, thereby resulting in inefficiencies and wasted product. In particular, the internal volume of the interconnecting pathways between the barrels and the applicator tip represents the volume of the components that will fail to be mixed or discharged from the syringe, and will therefore be wasted.

Yet another problem with integrally connected double barrel syringes is that they are often manufactured out of a single type of material, such as during an injection molding process. This may be economical for manufacturing purposes, but it can also preclude the use of certain inexpensive or desired materials. For instance, by way of example and not limitation, if it is desired to manufacture the syringe out of a transparent material but one component is photosensitive, the double barrel syringe cannot be manufactured out of a transparent material or else the one component will prematurely cure, even when the other component is not photosensitive. Likewise, if the one component adversely reacts with a certain type of material, that certain type of material cannot be used to manufacture the double barrel syringe, even if it will not react with the other component.

Accordingly, in view of the foregoing, there is currently a need in the art for improved dispensing devices and, more particularly, to syringe devices configured to dispense mixed compositions in a quick and convenient manner, while preserving the appropriate mixing ratios of the composition and while reducing any losses associated with transferring the components to an applicator tip. It would also be an advancement in the art to provide such improved syringe devices that have barrels that can be manufactured out of different materials to accommodate the different characteristics of the components that are contained therein.

SUMMARY OF PRESENTLY PREFERRED EMBODIMENTS

Briefly summarized, presently preferred embodiments of the present invention are directed to improved syringe devices that are capable of dispensing the components of a mixed composition in appropriate proportions and of mixing the components prior to being dispensed. The syringe devices of the invention are also configured with tips that can be placed adjacently or in close proximity to reduce any losses associated with transferring the components to a mixing tip, while enabling the barrels to be filled from their tips. Certain improved syringe devices of the invention also include barrels that can be manufactured out of different materials to accommodate and preserve the different characteristics of the components that are contained within the barrels of the syringe devices.

According to one embodiment, the syringe devices of the invention include two barrels that are each configured for containing one of the two components of a mixed composition. The syringe devices also include barrel connecting means for detachably connecting the barrels. Barrel connecting means are useful for at least enabling the barrels to be separated so they can be filled from their front ends, regardless of the proximity of the barrel tips once the syringe device is completely assembled. Front filling the barrels with the corresponding components is also particularly useful for reducing any chance that bubbles or other pressure irregularities will be formed within the barrels during the filling process. In particular, the plunger can be pushed all the way into the barrel, expelling all the air, then retracted while the components are loaded from the tip. In contrast, backfilling requires the plunger to be inserted after filler, such that air can be introduced into the barrel during insertion of the plunger.

Barrel connecting means are also useful for enabling the barrels to be connected after filling to ensure the two components are dispensed in appropriate proportions, such as, for example, by a plunger assembly configured to simultaneously dispense the components from the two connected barrels. Barrel connecting means can include any combination of interesting ridge formations, snap formations, friction fitting stem and slot formations, an applicator tip, an applicator tip retaining collar, and the plunger assembly.

The plunger assembly generally includes two plungers that are configured for simultaneously expressing the first and second components out from the barrels. The plunger assembly also includes plunger coupling means for detachably coupling the first and second plungers together, which is useful for enabling the plungers to be separated without having to remove the plungers from the barrels, such as, for example, when the barrels are separated for filling. Plunger coupling means includes any combination of interesting ridge formations, snap formations, plunger caps, and friction fitting stem and slot formations.

According to one embodiment of the invention, the syringe device also includes an applicator tip configured to thoroughly mix and dispense the components contained in the barrels. The applicator tip is also configured for being placed over the tips of the barrels, which are disposed adjacently or in close proximity to minimize any losses associated with transferring the components to the applicator tip. According to one embodiment, the applicator tip includes internal mixing vanes specifically configured to ensure the components are thoroughly mixed before they are dispensed from the syringe device. The applicator tip is secured to the tips of the barrels with a retaining collar that is placed around the applicator tip and secured to structure on the barrels.

According to one embodiment of the invention, the barrels of the syringe device comprise at least one of different inner diameters, different colors, different transmissiveness and different material compositions. This embodiment is useful for enabling the barrels to be manufactured with desired materials, attributes and/or shapes to accommodate and preserve the different attributes of the components contained within the barrels. This is particularly useful, for example, to prevent premature curing of the individual components. This embodiment is also useful when the appropriate mixing ratios of the components are not one to one, in which case the barrels can be manufactured with different inner diameters to accommodate and preserve the appropriate mixing ratio of the desired composition.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
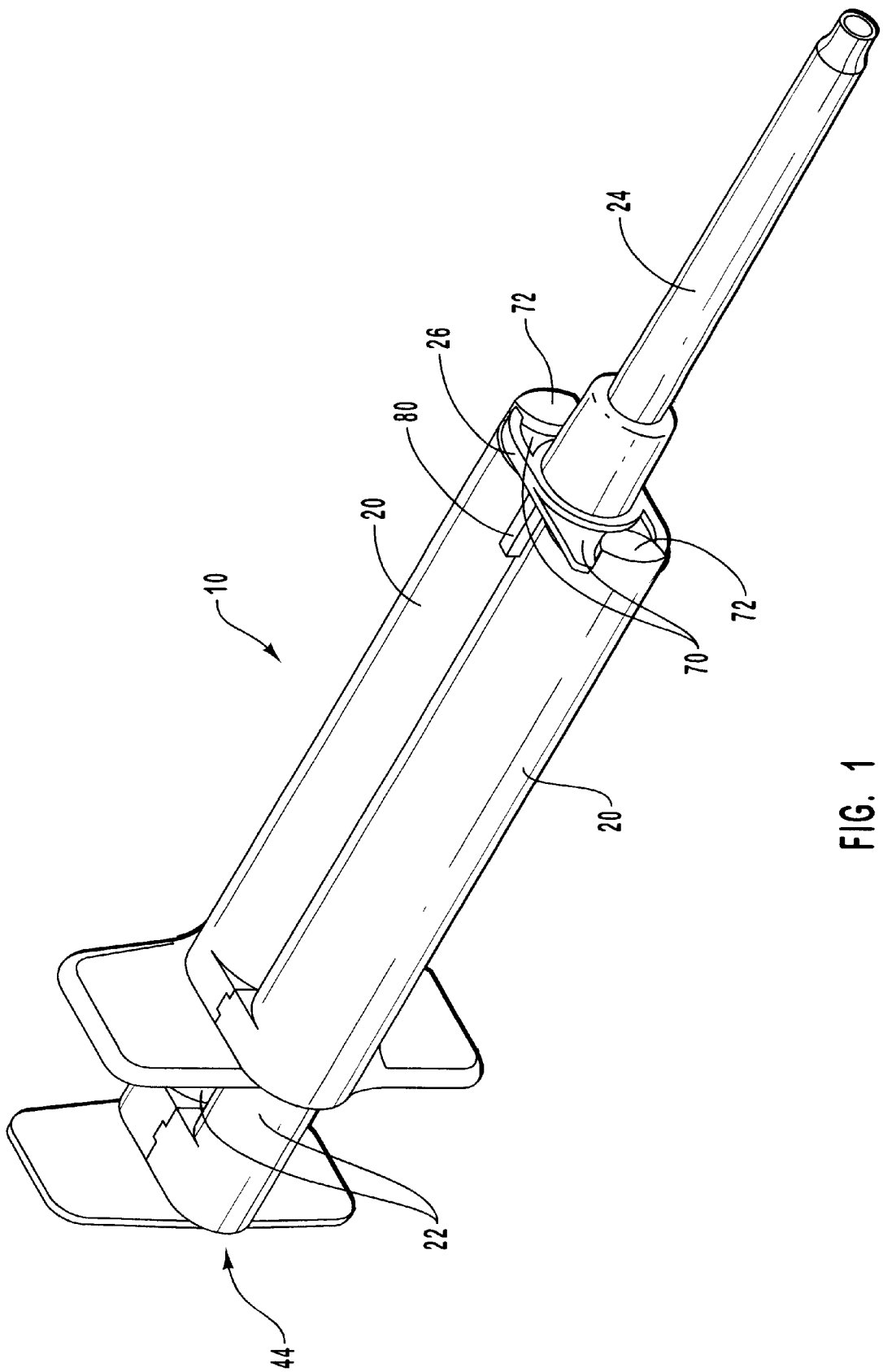
FIG. 1 illustrates a perspective view of one presently preferred embodiment of the syringe device of the invention that includes two detachably connecting barrels, two detachably connecting plungers of a plunger assembly, and an applicator tip.

A detailed description of the syringe device of the invention will now be provided with specific reference to figures illustrating preferred embodiments of the invention. It will be appreciated that like structures will be provided with like reference designations. To help provide context for understanding the scope of invention, certain terms used throughout the application will now be defined.

The term "component," as used herein, refers to any combination of synthetic and organic elements, solutions, and compounds. The components referred to herein preferably have a suitable viscosity for being discharged from a syringe and for being mixed with at least one other component to form a mixed composition. By way of example and not limitation, the components referred to herein may include the A and B components of dental resins, cements, composites and epoxies.

The term "mixed composition," which is sometimes used interchangeably herein with the terms "resultant composition" and "composition," is defined as a mixture of two components. According to one preferred embodiment, the mixed compositions include mixtures of complementary A and B components that undergo a chemical reaction when they are thoroughly mixed and which causes the mixed composition to cure in some desired manner. It will be appreciated, however, that the mixed compositions described herein are not limited to compositions that cure solely upon mixing the corresponding components of the mixed composition. In particular, the mixed compositions may also include compositions that cure upon contacting, being treated with, interacting with, or receiving another component, another composition, light, heat, or another curing element.

The term "thoroughly," which is used herein in reference to the mixing of the components of a mixed composition, means adequately for obtaining a desired result such as, for example, enabling the resultant composition to undergo a chemical reaction, for enabling the composition to cure in a desired manner, or for providing the composition with desired characteristics for interacting with another component, composition, or element. Inasmuch as different mixed compositions may require different levels of mixing involvement before obtaining the desired result, the term "thoroughly," should be construed in view of the composition being mixed and the desired result.

The terms "appropriate proportion" and "appropriate mixing ratio," refer to the mixing ratio of the components of a mixed composition that is appropriate for providing the resultant composition, upon being mixed thoroughly, to obtain the desired result.

The term "transmissiveness," as defined herein, refers to the opaque or transparent attributes of a material, with specific reference to the opaque or transparent attributes of the materials composing the barrels of the syringe devices of the invention.

As described herein, certain syringe devices of the invention are generally capable of dispensing components of a mixed composition in appropriate proportions and for thoroughly mixing the components prior to being dispensed. In some embodiments, the syringe devices also include barrels having different characteristics to accommodate and preserve the different properties of the components that are contained within the barrels of the syringe devices.

FIG. 1 illustrates one presently preferred embodiment of the syringe device 10 of the invention. As shown, the syringe device generally includes two barrels 20 that are each configured for containing one of the two components of a mixed composition, two plungers 22 that are sized and configured for forcibly expressing the components out from the corresponding barrels 20, an applicator tip 24 configured for mixing and dispensing the resultant mixed composition, and a retaining collar 26 configured for securing the applicator tip to the barrels. Each of these objects will now be described in detail.

Figure 2:
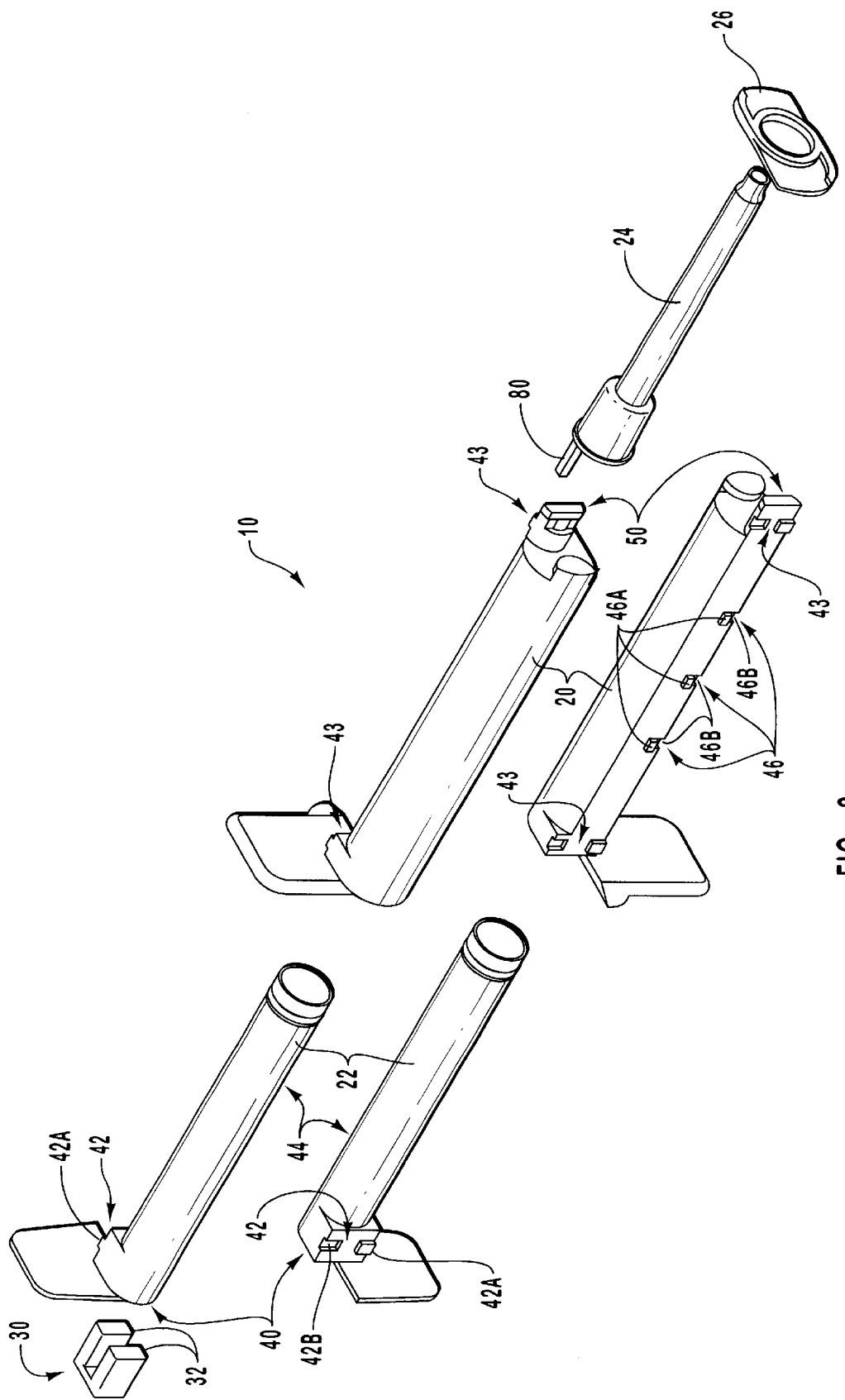
FIG. 2 illustrates a perspective exploded view of one presently preferred embodiment of the syringe device of the invention that shows two plungers, two barrels, a plunger cap, an applicator tip and a retaining collar.

FIG. 2 illustrates an exploded view of the syringe device 10, which more clearly shows the plungers 22, barrels 20, applicator tip 24 and retaining collar 26 of the syringe device 10. As shown, the syringe device 10 may also include a plunger cap 30 that is configured for detachably connecting the plungers 22 together. In particular, the plunger cap 30 includes two protruding members 32 that are sized and configured for being inserted within corresponding recesses (not shown) formed in the back ends 40 of each plungers 22. In this manner, the plunger cap 30 comprises plunger coupling means for detachably connecting the plungers 22.

In another embodiment, the valve syringe 10 includes plunger coupling means comprising structure that is integrally formed into each of the plungers 22 and which is configured to detachably connect the plungers 22. For example, in the present embodiment, tongue and groove slot formations 42 comprise structure configured to detachably connect the plungers 22, wherein a protrusion 42A and a groove 42B on each plunger 22 are configured to mate and frictionally engage the protrusion 42A and groove 42 on the opposing plunger 22 for detachably connecting the plungers 22. However, only one of the grooves 42B is presently visible. The plunger coupling means can also include the plunger cap 30.

Despite the aforementioned examples of plunger coupling means, it will be appreciated, that the plunger coupling means is not limited to any particular structure. In particular, the plunger coupling means may also include, but is not limited to any combination of interesting ridge formations, snap formations, and friction fitting stem and slot formations.

The plunger coupling means, as they have been described, are useful for at least enabling the plungers 22 to be connected during use so that they can simultaneously express the components from both of the barrels 20. This is useful, for example, to ensure the components are expressed in the appropriate mixing ratios for obtaining the desired mixed composition. The plunger coupling means are also useful for allowing the plungers 22 to be separated along with the barrels 20 so they can be filled from the front, which, as described above, is useful for reducing the chances that pressure irregularities will be formed within the barrels 20 during the filling process.

In certain embodiments, it is desirable that the plungers 22 of the plunger assembly are fixedly attached. In these embodiments, the plungers 22 can be integrally connected together during manufacture, such as during a 2-color molding process, or subsequent the manufacturing process, such as with an adhesive, welding, or a mechanical coupling.

Figure 3:
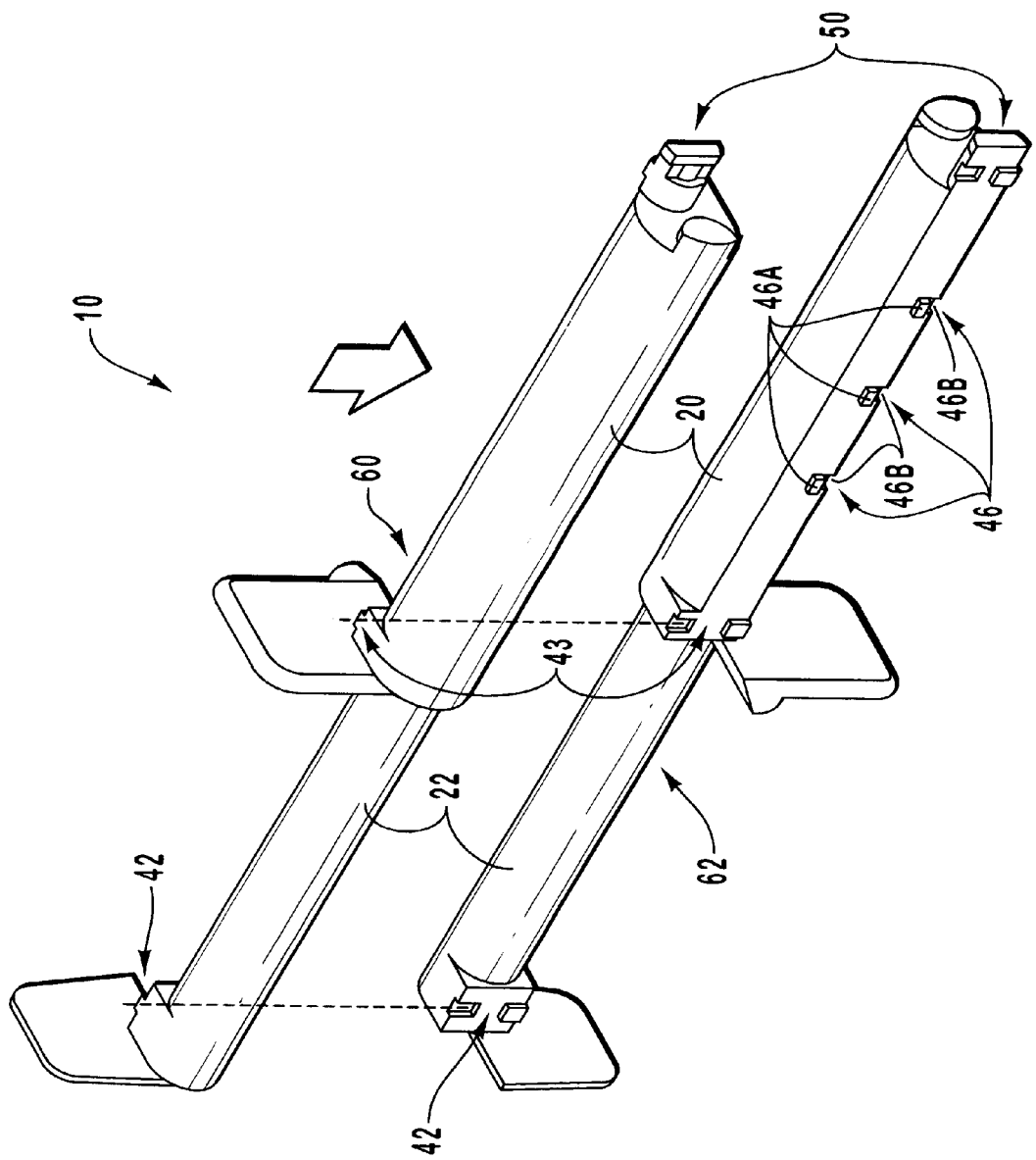
FIG. 3 illustrates one embodiment of a partially assembled syringe device of the invention that includes two plunger and barrel subassemblies, barrel coupling means and plunger coupling means configured to be detachably connected.

According to one presently preferred embodiment, the syringe devices 10 of the invention also include barrel coupling means for detachably connecting the barrels 20. As shown in FIGS. 2 and 3, barrel coupling means for detachably coupling the barrels 20 may include structure such as, but not limited to, the tongue and groove formations 43 and the tab and slot formations 46, which are correspondingly formed into each of the barrels 20, although the tab and slot formations can only be seen on one of the barrels 20 in the present illustration. Other non-limiting examples of barrel coupling means include combinations of interesting ridge formations, snap formations, and friction fining stem and slot formations. One attribute of the barrel coupling means of the invention is that they are able to hold the barrels 20 in fixed relative alignment. In particular, the barrel coupling means effectively prevent the barrels 20, once connected, from rotating or sliding with respect to each other. It will be appreciated that this is useful for enabling the plunger assembly 44 to simultaneously express the contents from each of the barrels 20, which would not be possible if the barrels 20 are free to move relative to one another during use.

According to one embodiment, the barrel connecting means for detachably connecting the barrels 20 includes the plunger assembly 44, which is generally described above to include the two detachably connecting plungers 22. In particular, when the plungers 22 are connected, they are able to provide support to the barrels 20 for helping hold the barrels 20 together.

Figure 4:
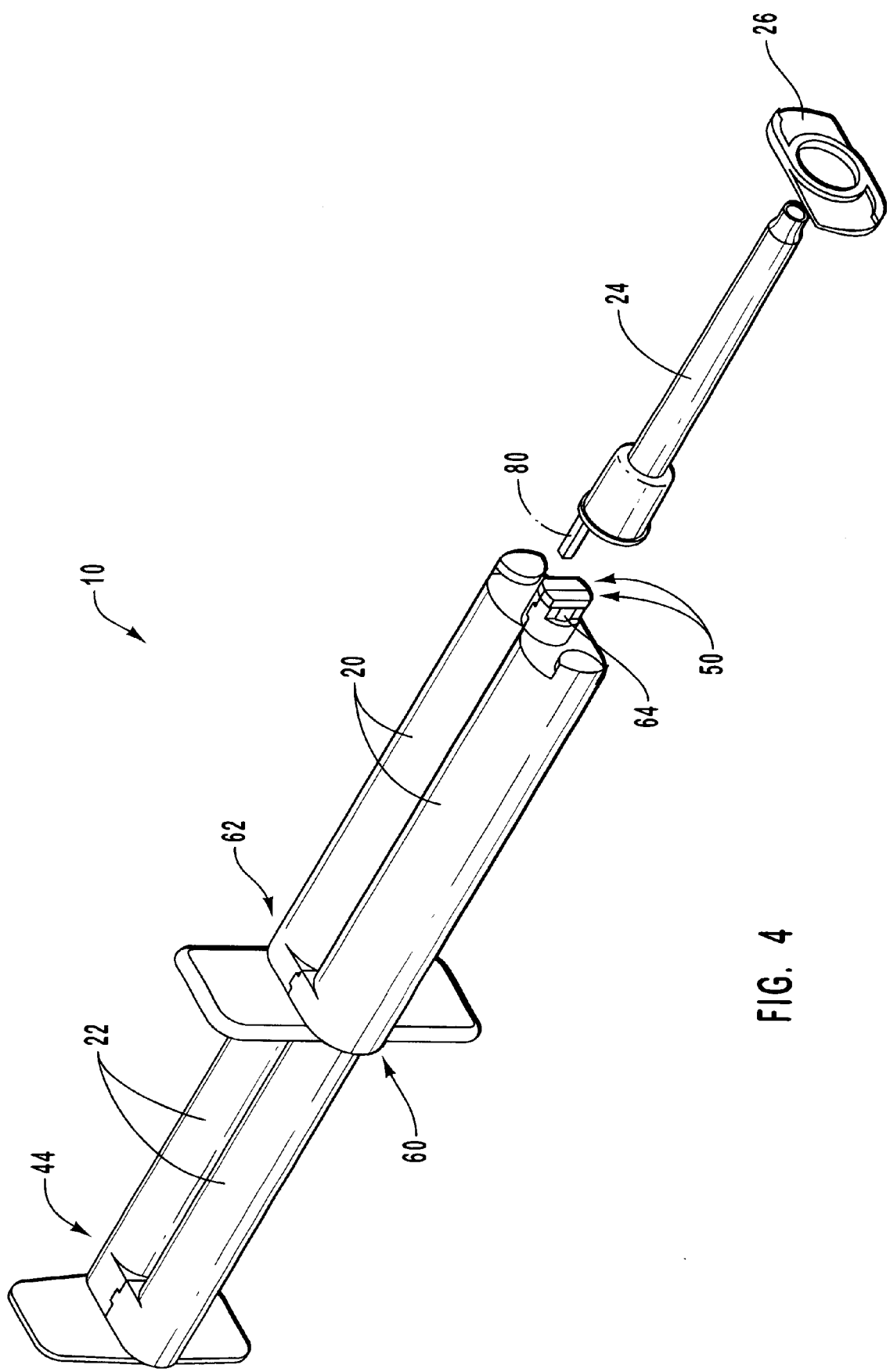
FIG. 4 illustrates the two plunger and barrel subassemblies shown in FIG. 3 that are detachably connected and with an applicator tip in position for being placed over the adjacently disposed tips of the barrels.

According to yet another embodiment, the barrel coupling means includes the applicator tip 24, which is configured for being placed over the dispensing ends or tips 50 of the barrels 20. Although the applicator tip 24 is primarily configured to mix and dispense the components contained in the barrels 20, as described below, it can also be used to detachably connect the barrels together when it is secured in placement over the tips 50 of the barrels 20. To facilitate placement of the applicator tip 24 over the dispensing tips 50 of the barrels 20, it is preferred that the tips 50 of the barrels 20 are located adjacently, or at least in close proximity when the barrels are connected, as shown in FIG. 4. The proximity of the dispensing tips 50 is also particularly useful for minimizing the distance the components must travel before being dispensed from the syringe device 10, and thereby reducing any losses associated with transferring the components to the applicator tip 24. The applicator tip 24 is secured to the dispensing tips 50 of the barrels 20 with a retaining collar 26, as generally described below in reference to FIGS. 5–7.

Figure 5:
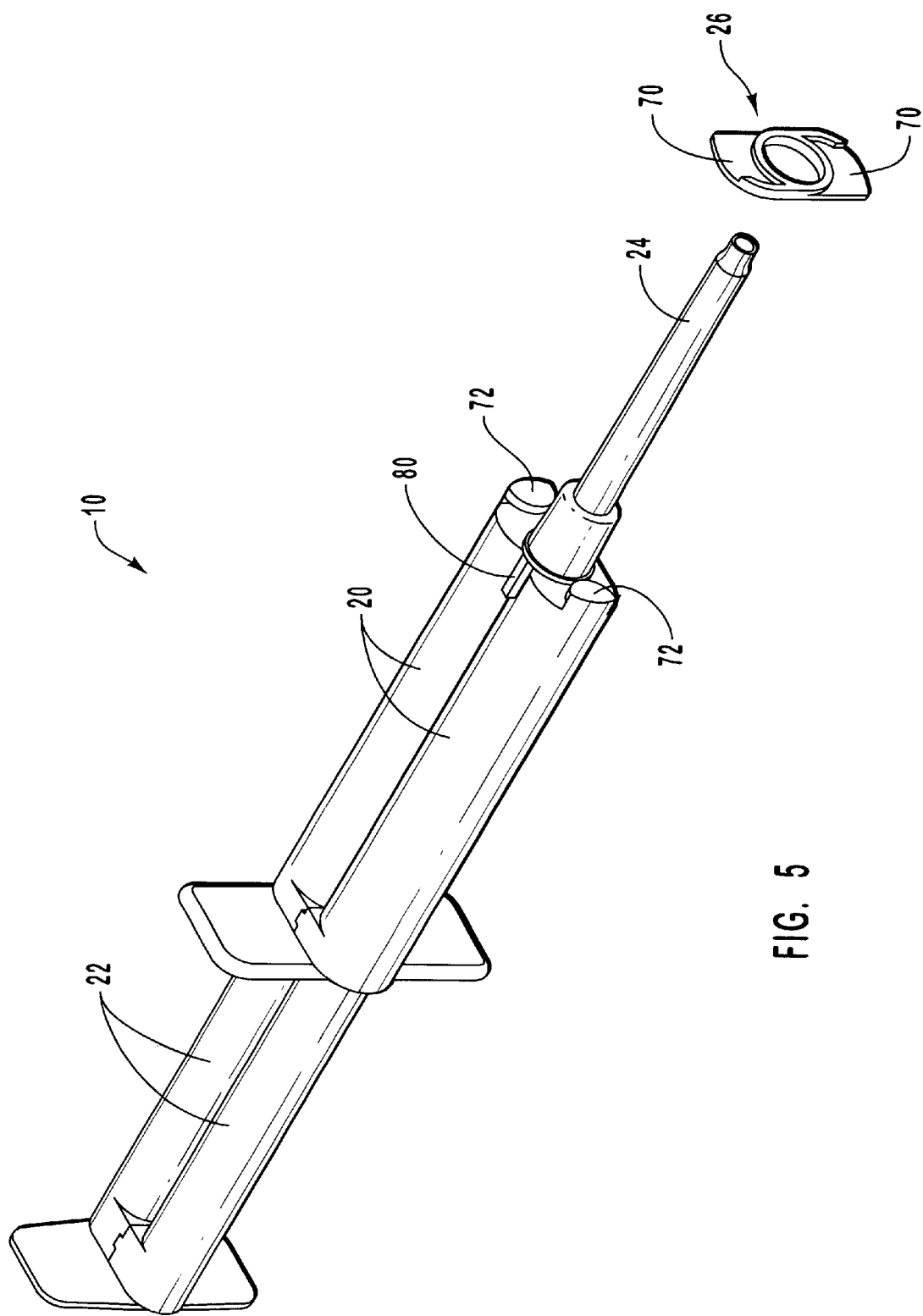
FIG. 5 illustrates the syringe device of FIG. 4 in which the applicator tip is connected to the barrels and in which a retaining collar is in position for being placed over the applicator tip.

Attention is now directed to FIGS. 3–5 for explaining methods for assembling and using the syringe devices 10 of the invention. As shown in FIG. 3, each of the plungers 22 is sized and configured for being inserted into a corresponding barrel 20. To further interconnect the plungers 20 and barrels 22, one of the plunger and barrel subassemblies 60 is positioned above the other plunger and barrel subassembly 62 in a position that aligns that the tongue and groove formations 42 and 43 in the first subassembly 60 with the tongue and groove formations 42 and 43 in the second subassembly 62. Next, the subassemblies 60 and 62 are moved together in a manner that enables the tongue and groove formations 42 and 43 from the first subassembly 61 to slidably engage and internest with the tongue and groove formations 42 and 43 in the second subassembly 62.

Once the subassemblies 60 and 62 are completely connected then the tab and slot formations 46 engage to further prevent the subassemblies from unintentionally becoming disconnected. In particular, the tab and slot formations 46 are correspondingly formed in each of the barrels 20, although they are only visible in the barrel 20 of subassembly 62, so that a small tab 46A on each of the tab and slot formations 46 will engage a corresponding recess 46B on the opposing barrel 20. When the barrels 20 are connected, as described above, then each tab 46A is engaged within a corresponding recess 46B on the opposing barrel 20, thereby interlocking and preventing the barrels 20 from inadvertently becoming disconnected during periods of use and nonuse.

When it is desired to disconnect the barrels 20 such as, for example, to refill the barrels 20 or to use the subassemblies 60 and 62 separately, then the barrels 20 can be separated by applying a sufficient force to the barrels 20, while pulling the barrels 20 apart, to overcome the retention capabilities of the tab and slot formations 46. In some embodiments, however, it is desirable to fixedly connect the subassemblies 60 and 62 together so that they cannot be detached. This can be accomplished, for example, with adhesives, by welding, or by mechanical means, such as by increasing the size and interlocking capabilities of the tab and slot formations 46.

FIG. 4 illustrates the syringe device 10 of the invention in which the subassemblies 60 and 62 have been connected and in which an applicator tip 24 is in positional alignment for being placed over the barrel tips 50. As shown, the tips 50 of the barrels 20 are disposed adjacently, which is useful, for facilitating the placement of the applicator tip 24 over the barrel tips 50 and for minimizing the distance the components within the barrels 20 have to travel before entering the applicator tip 24.

During use, the components within the barrels 20 are expressed out of holes 64 that are formed in each of the barrel tips 50, although only one is visible, when the plunger assembly 44 is forced towards the barrels 20. The expressed components can be dispensed directly out of the barrel tips 50 or, alternatively, the components can be dispensed through the applicator tip 24. To dispense the components directly out of the barrel tips 50, the syringe device 10 is used without an applicator tip 24.

To dispense the components out of the applicator tip 24, it is first necessary to secure the applicator tip 24 over the barrel tips 50 so that it can receive and dispense the components from the barrels 20. One benefit of using the applicator tip 24 is that it initiates the mixing of the components before they are dispensed, which is generally useful for minimizing the time and mess associated with external mixing processes. In certain preferred embodiments, the applicator tip 24 is able to thoroughly mix the components so as to eliminate the need for subsequent mixing upon dispensing the composition. Depending on the mixing requirements for different compositions, thorough mixing of the components can be accomplished, for example, with a simple applicator tip 24 having a hollow body or with more structurally complex applicator tips configured to provide involved mixing. Examples of mixing tips and tubes configured to provide involved mixing are described in U.S. Pat. No. 6,234,795, to Fischer, entitled "Flexible Mixer Extender," and U.S. patent application Ser. No. 09/802,027, filed Mar. 8, 2001, entitled "Multiple Material Dispensing Systems with Flexible Coupling Tubes," both of which are incorporated herein by reference.

FIG. 5 illustrates one embodiment for securing the applicator tip 24 to the tips of the barrels 20. As shown, a retaining collar 26 is configured with ledges 70 or other structure that is configured for engaging or otherwise interlocking with the ridges 72 or other structure formed in the barrels 20. For instance, once the collar 26 is completely placed onto the applicator tip 24 and against the barrels 20, in the alignment shown, the collar 26 can be rotated into the locking position that is shown in FIG. 1. In the locking position, the ledges 70 of the collar 26 are frictionally or otherwise mechanically engaged between the barrel ridges 72 and the bodies of the barrels 20. This frictional engagement effectively prevents the applicator tip 24 from being removed from the syringe device 10 until the collar 26 is sufficiently rotated in the opposite direction to slidably release the ledges 70 from under the ridges 72.

Figure 6:
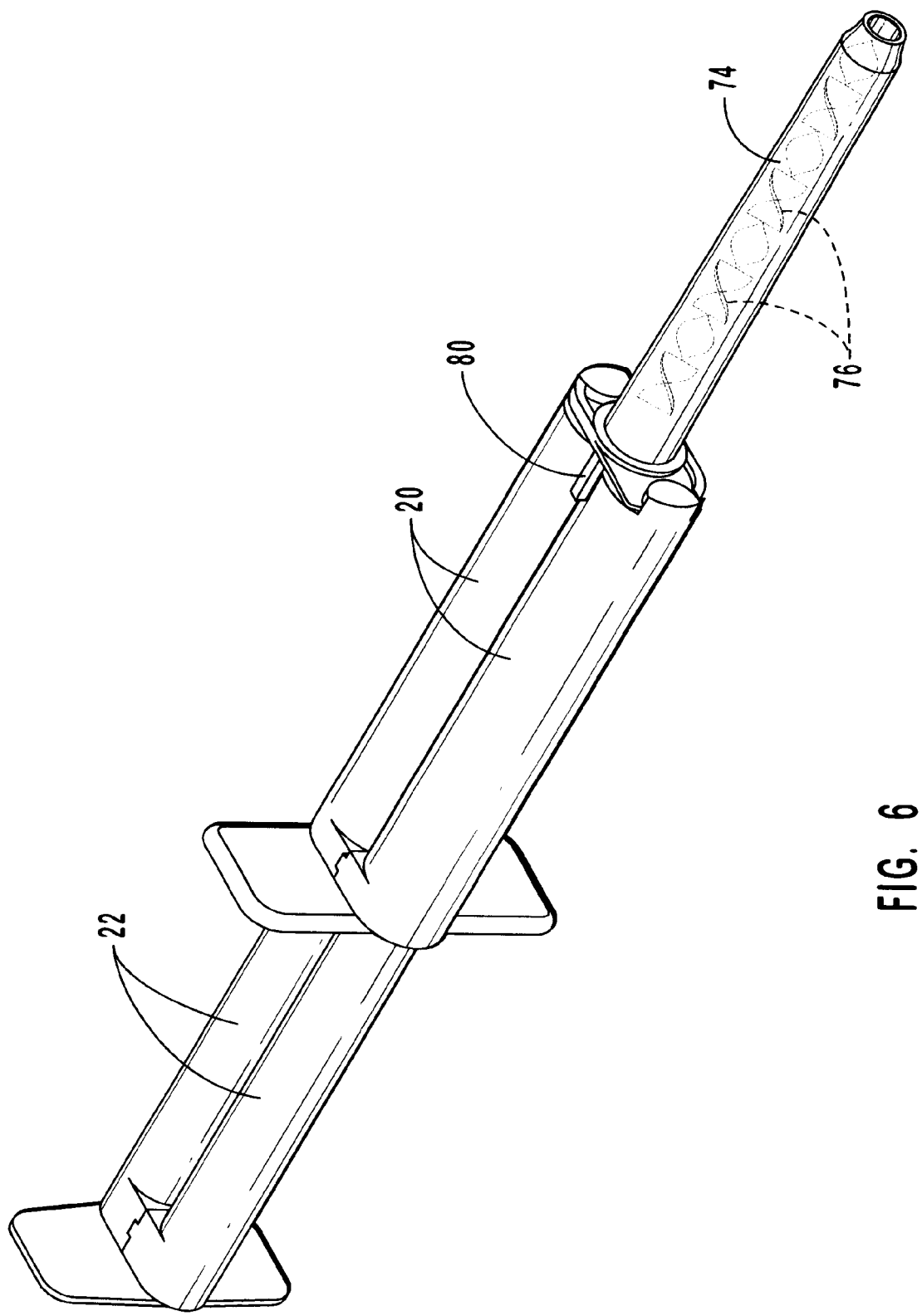
FIG. 6 illustrates a syringe device in which the applicator tip comprises a mixing tip having internal mixing vanes configured for thoroughly mixing the components within the barrels with a retaining collar securing the applicator tip on the end of the barrels.

According to one embodiment, illustrated in FIG. 6, the applicator tip 74 is configured for providing involved mixing of the components before they are expressed out of the barrels 20, as generally described above. This applicator tip 74 includes internal mixing vanes 76 that are configured to thoroughly mix the components before they are dispensed from the applicator tip 74.

One additional feature of the applicator tips 24 and 74 of the invention is that they include alignment means for securing the applicator tips 24 and 74 in a desired alignment with respect to the barrels 20 so that the applicator tips 24 and 74 do not rotate in a manner that would cause the components to cross-migrate or otherwise be introduced into the wrong barrels during periods of non-use and which could cause premature curing of the composition. To further prevent undesired cross-migration, the head of the applicator tip can be configured to prevent any mixing of the components until the components are forced into the main body of the applicator tip where the mixing vanes are located.

Although specific examples have been provided regarding certain embodiments of the applicator tips of the invention, it will be appreciated that the applicator tips may also comprise other embodiments and attributes that have not been discussed. For instance, by way of example and not limitation, the applicator tips can be rigid, flexible, curved, straight, tubular, tapered, and flocked to provide the syringe devices with any other desired functionality, in addition to thoroughly mixing the components of the desired composition.

In yet other embodiments, the syringe devices of the invention are used without an applicator tip. For instance, the functionality may include preserving the desired mixing ratios of the dispensed components or preventing the premature curing of the components within the barrels, without mixing the components, in which case the applicator tip is not required.

Figure 7:
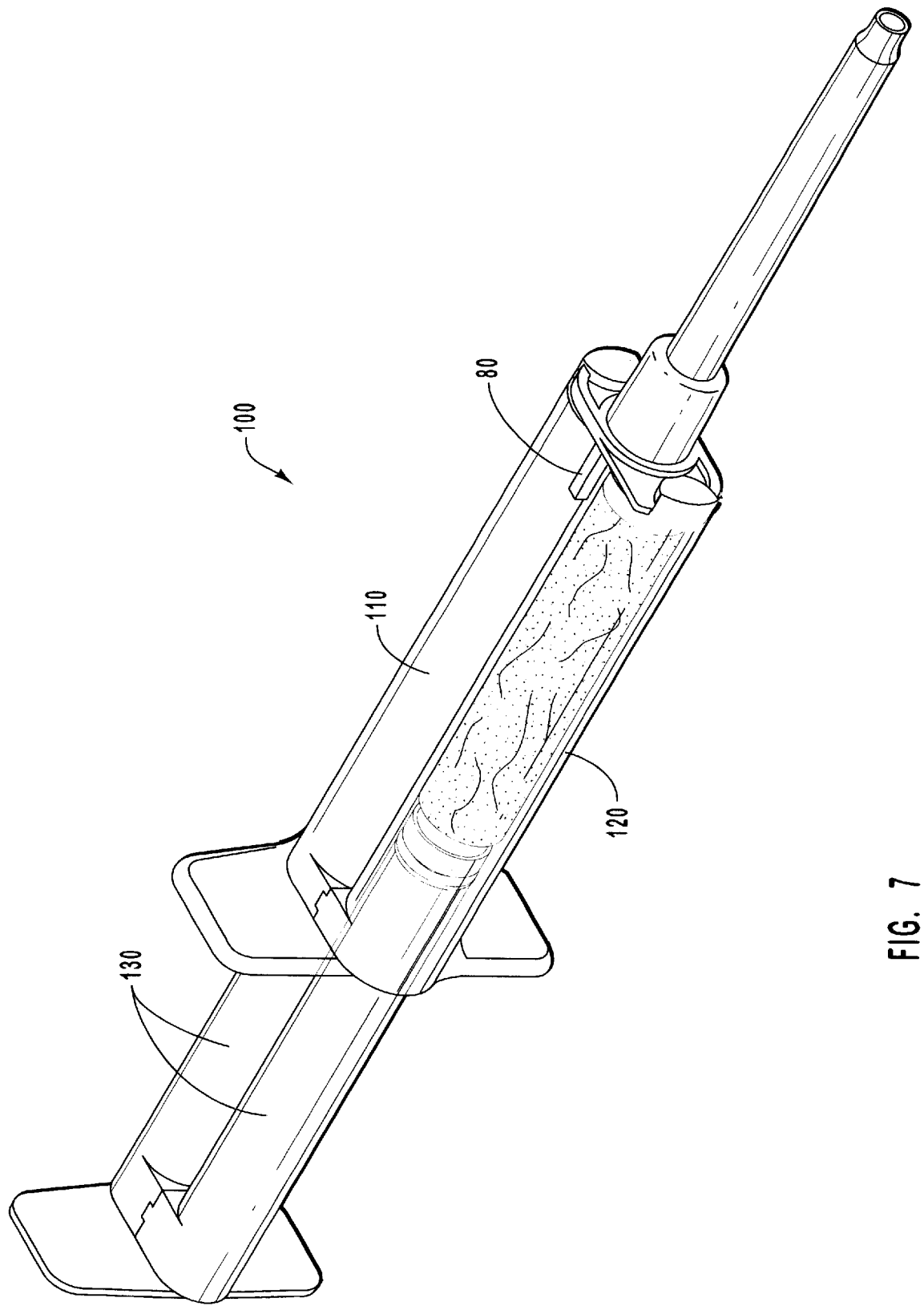
FIG. 7 illustrates one embodiment of the syringe device of the invention that includes one opaque barrel and one transparent barrel.
Figure 8:
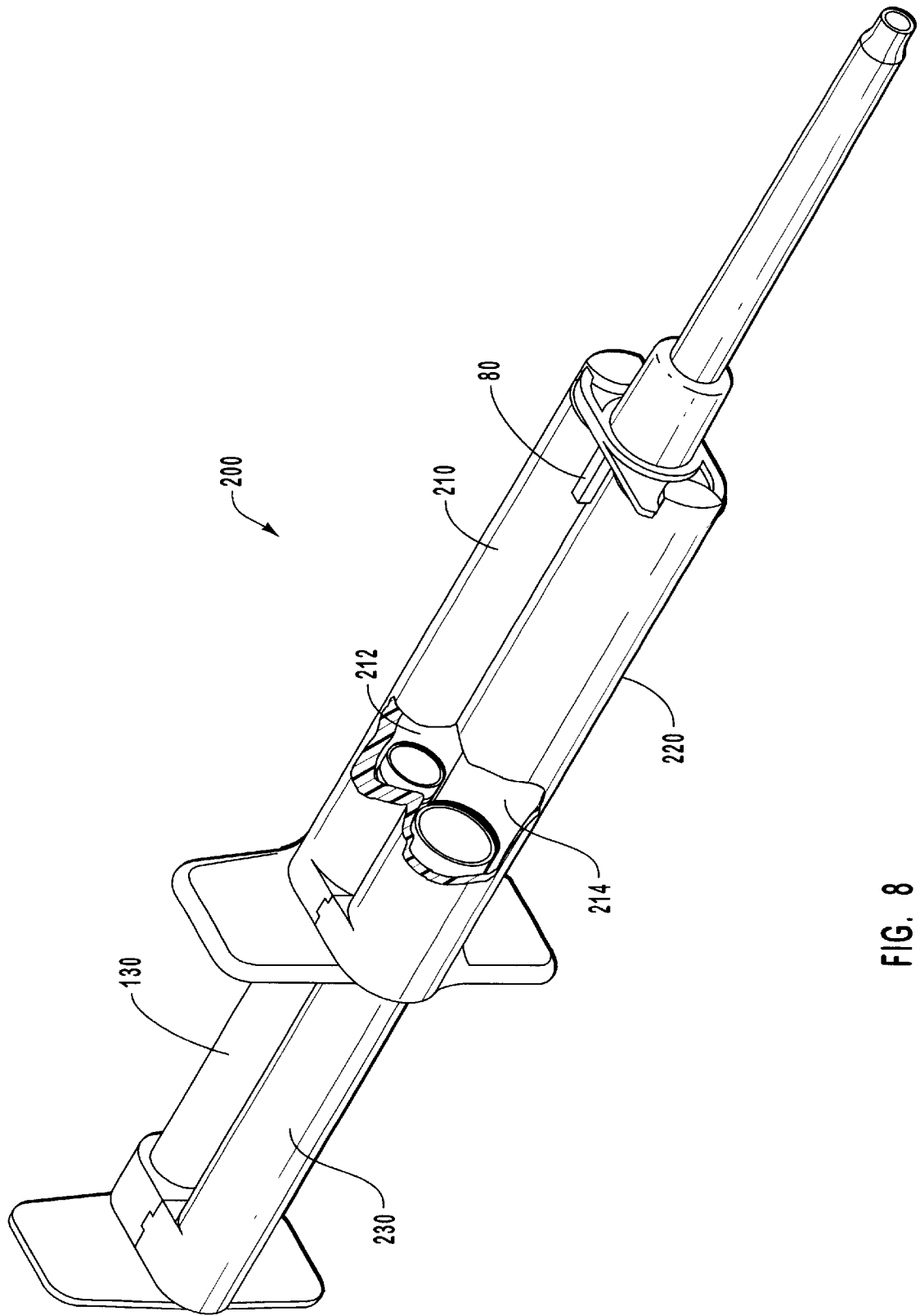
FIG. 8 illustrates one embodiment of the syringe device of the invention that includes one barrel having a first inner diameter and a second barrel having a second inner diameter that is different than the first inner diameter.

FIGS. 7 and 8 illustrate embodiments of the syringe devices 100 and 200 that are particularly amenable for preserving the desired mixing proportions of the dispensed components and for preventing premature curing of the components prior to being dispensed.

As shown in FIG. 7, the syringe device includes a first barrel 110 that is opaque and a second barrel 120 that is transparent. This embodiment is particularly useful when the component contained within the first barrel 110 is photosensitive but it is desired to form the second barrel 120 out of a transparent material. It may be desirable to form the second barrel 120 out of a transparent material for marketing reasons or for enabling a user to know approximately how much of the component is left within the syringe device 100.

It will be appreciated that the barrel coupling means of the invention, as described above, enables the barrels 110 and 120 to be manufactured separately out of different materials such as, for example, to enable the first barrel 110 to be manufactured out an opaque material and to form the second barrel 120 out of a transparent material, while still enabling the first barrel 110 to preserve the component contained in the first barrel 110 from premature photo-curing and while still enabling the barrels 110 and 120 to be detachably connected for providing the utility of the invention, as described above. Although not shown, the transparent barrel 120 or plunger 130 may also be marked with dosage markings or other markings to indicate how much of the composition is being expressed as a result of forcing the plungers 130 through the barrels 110 and 120.

The utility of manufacturing the barrels separately also extends to other embodiments in which the components within the barrels 110 and 120 react differently to the materials of the barrels. For instance, the present invention enables the first barrel 110 to be composed of a material that is chemically reactive with the component contained within the second barrel 120, but which is not chemically reactive with the component contained in the first barrel 110. According to this embodiment, the second barrel 120 can also be composed of a second material composition that is non-reactive with the component contained in the second barrel 120, thereby enabling the syringe device 100 to preserve the desired characteristics of the second component, despite manufacturing the first barrel 110 out of a material that undesirably reacts with the second component. It can also be desirable, in certain circumstances, to manufacture barrels out of different materials for economic reasons or marketing reasons.

In another embodiment the barrels of the syringe device compose different colors or tinting, which can be useful for preventing undesired frequencies of light from penetrating the barrel chambers and for marketing reasons, such as for example, to identify different products within the barrels of the syringe device.

In yet another embodiment, the barrels of the syringe device comprise different insulating properties, which can be useful for protecting the refrigent characteristics of certain components contained within the barrels. In summary, the syringe devices of the invention can include detachably connecting barrels that are manufactured out of different materials for any number of reasons, while still preserving the utility provided by the invention.

FIG. 8 illustrates yet another embodiment of the syringe device 200 of the invention. In this embodiment, the barrels of the syringe device 200 comprise different shapes. In particular, the first barrel 210 has a smaller inner diameter 212 than the inner diameter 214 of the second barrel 220. The plungers 230 and 240 are also sized and configured to correspondingly fit within the barrels 210 and 220, respectively, and to forcibly express the components (not shown) out from the barrels 210 and 220. It will be appreciated that this embodiment is particularly useful when the appropriate mixing ratio of the desired mixed composition requires a greater proportion of the component contained within the second barrel 220 than the component contained in the first barrel 210, or vice versa.

In summary, the syringe devices of the invention include detachably connected barrels that can be manufactured with different materials and shapes to preserve and accommodate the different properties of the components contained within the barrels. This is useful, for example, to prevent premature curing and to accommodate the mixing ratios and properties of the components contained within the barrels. The barrel coupling means of the invention are also useful for enabling the detachably connecting barrels to be front filled, as opposed to back filled, for reducing any chance that bubbles or other pressure irregularities will form within the barrels during the filling process. Another benefit of the invention is that the plunger assembly includes plunger coupling means for coupling the plungers together and for ensuring the contents are simultaneously dispensed from the barrels in an appropriate manner for maintaining the desire mixing ratios. Yet another benefit of the invention is that the applicator tip can be configured to thoroughly mix the components before they are discharged so as to eliminate the need for subsequent mixing procedures that are messy and time consuming.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A syringe device, comprising:
   first and second barrels detachably connected together and configured for containing respective first and second components,
      the first and second barrels characterized by at least one of (i) being composed of different materials, (ii) being of different colors, (iii) one being opaque and another being translucent, or (iv) having different insulating properties;
   a plunger assembly having a first plunger configured for forcibly expressing the first component out from the first barrel and a second plunger configured for forcibly expressing the second component out from the second barrel; and
   an applicator tip configured to mix and dispense the first and second components when the first and second components are expressed out from the first and second barrels.

2. A syringe device as recited in claim 1, the applicator tip, when connected to a dispensing tip of each of the first and second barrels, assists in locking the first and second barrels together.

3. A syringe device as recited in claim 2, further comprising a retaining collar configured to securely connect the applicator tip with the dispensing tip of each of the first and second barrels.

4. A syringe device as recited in claim 1, wherein each of the first and second plungers comprises plunger coupling means for detachably coupling the first and the second plungers together.

5. A syringe device as recited in claim 1, wherein the first and second plungers of the plunger are integrally connected together and assist in connecting the first and second barrels together when inserted therein.

6. A syringe device as recited in claim 1, wherein the applicator tip includes internal mixing vanes configured to thoroughly mix the first and second components when the first and second components are expressed into the applicator tip.

7. A syringe device as recited in claim 1, wherein the first and second barrels are of different sizes.

8. A syringe device as recited in claim 1, wherein the first and second barrels are colored differently and wherein the first barrel is suitably colored to prevent premature photocuring of the first component.

9. A syringe device as recited in claim 1, wherein the first and second barrels are composed of different materials and wherein the material of the first barrel is non-reactive with the first component and reactive with the second component.

10. A syringe device as recited in claim 1, wherein the first and second barrels further comprise barrel connecting means which comprise at least one of internesting ridge formations, snap formations, and friction fitting stem and slot formations.

11. A syringe device, comprising:
   first and second detachably connecting barrels configured for containing respective first and second components;
   one or more protrusions integrally attached to and disposed on a side of one of the barrels;
   one or more recesses disposed in a side of another of the barrels and configured so as to selectively engage the one or more protrusions and permit selective locking and unlocking of the first and second barrels,
   the protrusions and recesses, when engaged so as to lock the first and second barrels, prevent relative axial movement of the first and second barrels;
   a plunger assembly having a first plunger configured for forcibly expressing the first component out from the first barrel and a second plunger configured for forcibly expressing the second component out from the second barrel, the first and second plungers being detachably coupled together; and
   an applicator tip configured to thoroughly mix and dispense the first and second components when the first and second components are expressed out from the first and second barrels.

12. A syringe device as recited in claim 11, wherein the first and second plungers are detachably coupled together by at least one of internesting ridge formations, snap formations, and friction fitting stem and slot formations integrally formed in the first and second plungers.

13. A syringe device as recited in claim 11, wherein the first and second barrels comprise at least one of different colors, different insulating properties, different compositions, and different light transmissivenesses.

14. A syringe device as recited in claim 11, wherein the first and second barrels each comprise a plurality of protrusions and recesses corresponding to protrusions and recesses of the other barrel.

15. A syringe device, comprising:
   first and second detachably connecting barrels configured for containing respective first and second components;
   a first dispensing tip, disposed at an end of the first barrel, having a first dispensing hole transverse to the first barrel through which the first component is expressed;
   a second dispensing tip, disposed at an end of the second barrel, having a second dispensing hole transverse to the second barrel through which the second component is expressed,
   the first and second dispensing holes being oriented in order for the first and second components to be expressed from the first and second barrels in opposite directions when the first and second barrels are connected together; and
   a plunger assembly having a first plunger configured for forcibly expressing the first component out from the first barrel and a second plunger configured for forcibly expressing the second component out from the second barrel.

16. A syringe device as recited in claim 15, further comprising an applicator tip configured to thoroughly mix and dispense the first and second components when the first and second components are expressed out from the first and second barrels.

17. A syringe device as recited in claim 15, wherein the first and second plungers comprise structure for detachably coupling the first and second plungers together.

18. A syringe device as recited in claim 15, further comprising:

one or more protrusions disposed on a side of one of the barrels; and one or more recesses, disposed on a side of another of the barrels, configured so as to selectively engage the one or more protrusions and permit selective locking and unlocking of the first and second barrels, the protrusions and recesses, when engaged so as to lock the first and second barrels, prevent relative axial movement of the first and second barrels.

19. A syringe device as recited in claim 15, wherein the first and second barrels comprise at least one of different colors, different insulating properties, different material compositions, and different light transmissivenesses.

20. A syringe device as recited in claim 15, wherein the first and second barrels each comprise a plurality of protrusions and recesses corresponding to protrusions and recesses of the other barrel.

* * * * *